(12) United States Patent
Schlaminger (10) Patent No.: US 8,675,185 B2
(45) Date of Patent: Mar. 18, 2014

(54) DETERMINATION OF HAEMOLYSIS OF A BLOOD SAMPLE USING GRADIENT ANALYSIS

(75) Inventor: Michael Schlaminger, Graz (AT)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 425 days.

(21) Appl. No.: 12/641,688

(22) Filed: Dec. 18, 2009

(65) Prior Publication Data

US 2010/0159500 A1 Jun. 24, 2010

(30) Foreign Application Priority Data

Dec. 19, 2008 (EP) ..................................... 08022111

(51) Int. Cl.
*G01N 33/48* (2006.01)
(52) U.S. Cl.
USPC .............................................................. 356/39
(58) Field of Classification Search
USPC .................................... 356/39–42; 435/287.1
See application file for complete search history.

(56) References Cited

U.S. PATENT DOCUMENTS

| | | | | |
|---|---|---|---|---|
| 4,040,742 | A * | 8/1977 | Ito et al. ........................... | 356/39 |
| 4,813,420 | A | 3/1989 | Nunogaki | |
| 5,260,598 | A | 11/1993 | Brass et al. | |
| 6,268,167 | B1 | 7/2001 | Wild et al. | |
| 6,330,058 | B1 * | 12/2001 | Garcia-Rubio et al. ........ | 356/39 |
| 8,026,101 | B2 * | 9/2011 | Bower et al. ..................... | 436/43 |
| 2002/0167667 | A1 * | 11/2002 | Samsoondar et al. ........ | 356/436 |
| 2005/0051466 | A1 | 3/2005 | Carter et al. | |
| 2008/0261262 | A1 * | 10/2008 | Godfrin ........................... | 435/30 |
| 2008/0297769 | A1 * | 12/2008 | Bamberg et al. ................ | 356/73 |

FOREIGN PATENT DOCUMENTS

| | | |
|---|---|---|
| CN | 1809739 A | 7/2006 |
| DE | 1295888 B1 | 5/1969 |
| EP | 0268025 A | 5/1988 |
| JP | 4-151541 A | 5/1992 |
| WO | 2005003738 A2 | 1/2005 |

OTHER PUBLICATIONS

Pazdzior Grzegorz et al., "The kinetics of haemolysis of spherocytic erythrocytes", Cellular & Molecular Biology Letters, [online] vol. 8, No. 3, 2003, pp. 639-648.

(Continued)

*Primary Examiner* — Tarifur Chowdhury
*Assistant Examiner* — Michael P Lapage
(74) *Attorney, Agent, or Firm* — Thomas E. Lees, LLC (57) ABSTRACT

A determination of the haemolysis of a blood sample is provided by a measuring light source, a detector and an evaluation device. The light source irradiates the blood sample after a haemolysis operation on the blood sample has been started. The detector device detects light values at several measuring points of time. The evaluation device receives the detected light values and forms a time-dependent course of light values. The evaluation device also determines, at least sectionwise, a gradient for an assigned measuring curve from the time-dependent course of light values, as a comparative measure of the light values at the different measuring points of time. The evaluation device further determines when the gradient is different from zero, and indicates a conclusion of the haemolysis when the gradient, after a measuring period of time in which the gradient is different from zero, falls to a minimum going down to zero.

9 Claims, 10 Drawing Sheets

(56) References Cited

OTHER PUBLICATIONS

F. Neudel et al., "Effect of hemolysis on oxygen and hematocrit measurements by near infrared reflectance spectroscopy", Medical Engineering & Physics, Elsevier UK [online] vol. 24, No. 4, May 2002, pp. 301-307.

Scott, L. A., "Diffusion Across a Sheep Red Blood Cell Membrane", 1993, pp. 115-140, in Tested studies for laboratory teaching, vol. 14 (C.A. Goldman, Editor). Proceedings of the 14th Workshop/Conference of the Association for Biology Laboratory Education (ABLE), 240 pages.

Canadian Office Action dated Aug. 7, 2012, for Canadian patent application No. 2,688,757, for "Method for Determining the Haemolysis of a Blood Sample and Device".

Canadian Office Action dated Sep. 30, 2013, for Canadian patent application No. 2,688,757, for "Method for Determining the Haemolysis of a Blood Sample and Device".

English translation of Japanese Office Action dated Jun. 25, 2013, for Japanese patent application No. 2009-287493, see English translation of Notice of Reasons for Rejection and English translation of excerpt of Document 1.

* cited by examiner

DETERMINATION OF HAEMOLYSIS OF A BLOOD SAMPLE USING GRADIENT ANALYSIS

BACKGROUND OF THE INVENTION

The invention relates to techniques for determining the haemolysis of a blood sample and devices therefore.

So-called oximeters are used for determining constituents of blood samples. Here it concerns optical measuring devices with which total haemoglobin (tHb), haemoglobin derivates such as oxyhaemoglobin (O2Hb), carboxyhaemoglobin (COHb), methaemoglobin (MetHb) and the degradation product bilirubin are determined. These parameters are photometrically determined on the basis of the Lambert-Beer law. For this, usually the additive absorption of the individual components for several discrete wave lengths in the visible area is measured, for example between 459 nm and 666 nm. The determined measuring values form an over-determined linear equation system, which can be solved by means of a multi-linear regression to determine the concentrations concerned.

Measurement of the haemoglobin derivates takes place in the haemolysate, i.e., a haemolysed blood sample. This means that all dispersive corpuscular blood components such as erythrocytes and similar are completely destroyed as far as possible before the optical measuring value recording; that means haemolysed. The haemolysis of the blood cells takes place typically in that ultrasound is applied to the blood sample. On the basis of the medium homogenised in this manner, the Lambert-Beer law can be taken for actual determination of the concentration of the components which describes the constant weakening of light irradiated into the blood sample to be examined along its path through the blood sample.

In non-haemolysed condition, blood represents, in optical respect, a cloudy "colourful" particle-containing medium. Any light cast is weakened and dispersed depending on the wave length. Dispersal of the light takes place primarily on the cells located in the blood. The high degree of absorption of the short-wave blue light and the relatively low absorption of the red/infrared light through the blood emphasise the characteristic red colour of the blood. The various blood components influence the light absorption in characteristic wavelength ranges. The water contained in the blood absorbs infrared light above 1000 nm very intensively while proteins and haemoglobin preferably absorb in the green and blue spectral area.

In the non-haemolysed whole blood there is, alongside the absorption, dispersion and diffraction of the incidental light on the particles contained within it (above all on the cellular blood components). Due to the complexity of the dispersion method, conditioned above all by the form-conditioned high anisotropism and the bi-conclave cross-section and the variance of form of the erythrocytes, there is no analytically simply presentable connection between the concentration of the materials dissolved in the blood and the weakening of the light detected. To be able to carry out reproducible and informative optical measurements, the blood is therefore haemolysed.

When the blood has been completely haemolysed and if, in addition, all dispersing cell fragments have been removed, the light falling on the blood sample in the photometric examination is ideally exclusively absorbed by the components contained within it. The Lambert-Beer law can then be used for the determination of the concentration of the blood components.

Haemolysis is thus a significant prerequisite for subsequent photometric examination of blood samples. There is therefore a need for techniques for the determination of the haemolysis itself, in particular to create defined output conditions for subsequent examination of the haemolysed blood sample and thus to improve the accuracy and reproducibility of analytical examinations.

SUMMARY OF THE INVENTION

It is against the above background that the present invention provides certain unobvious advantages and advancements over the prior art. In particular, the inventor has recognized a need for improvements in methods for determining the haemolysis of a blood sample and devices.

Although the present invention is not limited to specific advantages or functionality, it is noted that the invention provides improved techniques for the determination of the haemolysis of a blood sample with which the haemolysis condition of the blood sample can be determined more closely.

In accordance with one aspect of the invention is a method for determination of the haemolysis of a blood sample during which the progress of the haemolysis is determined, wherein the method comprises the following steps:
  irradiation of the measuring light which is radiated from a measuring light source on the blood sample during haemolysis,
  detecting of measuring light values at several measuring points of time for measuring light transmitted through and/or reflected by the blood sample by means of a detector device,
  comparison of several of the measuring light values for different measuring points of time and determination of a measure for the haemolysis progress by means of an evaluation device by forming a time-dependent course for the measuring light values from the detected measuring light values and determining for the time-dependent course at least section-wise a gradient of an assigned measuring curve as a comparative measure for the comparison of the measuring light values at the various measuring points, and
  determination of the conclusion of haemolysis when the gradient within a selectable measurement accuracy, after a measuring period in which the gradient is different from zero, falls to a minimum going down to zero.

In the various forms of method execution it can be provided that the measure for the haemolysis progress is outputted with an output device. This can take place for all or individual measures of progress determined up to determination of the haemolysis section, for example by means of a notice on a display. Through this, a type of online haemolysis progress determination can be carried out for which continuously progress values are determined and displayed during the haemolysis. Alternatively, it is possible in the method not to output the method measures so that optionally only the end of haemolysis is displayed, for example with the aid of an optical and/or acoustic signal.

The gradient in the assigned measuring curve can be determined for individual points in the shape of the curve or also for curve sections running through several points of the curve. Positive and negative gradient values appear which show a rising and a falling shape of the curve.

With respect to determination of the haemolysis conclusion, it ensues that, in the non-haemolysed blood sample for the irradiated measuring light alongside absorption, dispersion and diffraction take place in embedded particles. If the blood, on the other hand, is completely haemolysed and if all dispersing cell fragments are removed, the incident measuring light is, in the ideal case, only absorbed. The transition between the condition of combined absorption, dispersion and diffraction for pure absorption is in the timely measuring curve shape recognisable as a transition between a gradient which is not zero and decreasing gradients of the measuring curve which, in the end, go up to a gradient of zero. When the gradient in the time course no longer changes, this shows that the haemolysis method, inasmuch as it concerns the current haemolysis, is concluded. The haemolysis section can be determined on reaching a zero gradient or before, if a characteristic change in the course of the gradient is detected.

In accordance with another aspect of the invention there is a method for determination of the haemolysis of a blood sample during which the progress of the haemolysis is determined, wherein the method comprises the following steps:

irradiation of the measuring light which is radiated from a measuring light source on the blood sample during haemolysis, detecting of at least one measuring absorption spectrum for measuring light transmitted through the blood sample by means of a detector device, comparison of at least one target absorption spectrum and the at least one measuring absorption spectrum for the blood sample in an evaluation device, determination of a measure for a haemolysis degree in comparing the at least one target absorption spectrum and the at least one measuring absorption spectrum, and output of an information signal derived from the measure for the haemolysis degree by means of an output instrument, which is functionally connected with the evaluation device.

The target absorption spectrum can be gained in various ways theoretically or experimentally which will be explained more closely below. It corresponds to an absorption spectrum for a known degree of haemolysis typically for a completely haemolysed blood sample. At least one measuring absorption spectrum is then measured for determination of haemolysis of the blood sample to be examined, to compare it with at least one target absorption spectrum.

In accordance with another aspect of the invention, a device for determination of the haemolysis of a blood sample is provided, which is configured to determine the progress of the haemolysis having:

a measuring light source which is configured to irradiate measuring light on the blood sample during haemolysis, a detector device which is configured to detect measuring light values at several measuring points of time for measuring light transmitted through and/or reflected by the blood sample, and an evaluation device which is configured to compare several of the measuring light values for different measuring points of time and to determine from this a measure for the haemolysis progress by forming, a time-dependent course for the measuring light values from the detected measuring light values and determining for the time-dependent course at least section-wise the gradient of an assigned measuring curve as a comparative measure for the comparison of the measuring light values at the different measuring points of time, and to determine a conclusion of the haemolysis when the gradient within a selectable measuring accuracy, after a measuring period in which the gradient is different from zero, falls to a minimum going down to zero.

In accordance with another aspect of the invention, a device for determination of haemolysis of a blood sample is provided and configured to compare the progress of the haemolysis by means of an evaluation device, which is configured to compare at least one target absorption spectrum and at least one measuring absorption spectrum for the blood sample and an output device, which is combined with the evaluation device and configured to output an information signal derived from the measure for the haemolysis degree.

The above-mentioned devices can be provided individually or in combination in a haemolysator.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

DETAILED DESCRIPTION OF THE INVENTION

The present invention is directed to improved techniques which enable reliable determination of haemolysis of a blood sample. Haemolysis of the blood sample can hereby be carried out in any desired manner or way using individual or several haemolysis methods which are known in various forms as such. It can thus be provided pressurising the blood sample, which is located in a measuring chamber, for haemolysis with ultrasound. Additionally or alternatively, haemolysis of the blood sample can be effected by means of the addition of one or more chemical reagents or through lowering the osmotic value of the blood sample.

In connection with the haemolysis progress determination, detection of the measuring light values for the measuring light transmitted through and/or reflected by the blood sample can take place continuously or discontinuously. No spectrally resolved measurement is provided in the haemolysis progress determination in a preferred form so that the measuring light values are detected free of any spectral assignment. Alternatively, though, wave-length-selective detection of the measuring light values can take place. This can be achieved in particular in that single-colour light is irradiated separately for several wave lengths and detected.

Determination of the measure for the haemolysis degree of the blood sample takes place typically spectrally resolved which means that target absorption values from at least one target absorption spectrum are correspondingly compared with measuring absorption values of their spectral assignment. For example, measuring values assigned to the same wave length can be compared with one another.

Determination of the haemolysis progress and determination of the measure for the haemolysis degree of the blood sample contribute to improved efficiency and optimised reproducibility in determining the blood sample. Additional effects result in their possible combination. For example, it can be provided that first of all to observe the progress of a haemolysis in order to determine subsequently from determination of the measure for the haemolysis degree whether there is sufficient haemolysis. If this is not the case, a subsequent haemolysis can be carried out for which then again the course is observed on the basis of haemolysis progress. Through this, additional information arises so that with greater security it can be established whether and in which scope the subsequent haemolysis contributes to an improvement of the haemolysing blood sample. On the other hand, determination of the measure for the haemolysis degree can be used parallel to the haemolysis to gain additional information about the degree of the currently proceeding haemolysis. In combined form, determination of the haemolysis progress and determination of the measure for the haemolysis degree thus increase improvements in the haemolysis determination of a blood sample achieved with the invention.

Typically, haemolysing of the blood sample takes place by means of the application of ultrasound directly on the blood sample located in a measuring cell. Compared with other haemolysis methods, for example, haemolysis through addition of a haemolysing reagent, no change in the composition of the blood sample takes place in the ultrasound haemolysis with the exception of lysing of the cell through additional reagents. This is, in particular, of advantage in case of any following analytical determination of the composition of the blood sample.

Typically, continued formation of the invention provides that the detection of measuring light values is carried out at least partly while a haemolysis operation of a haemolysis device used for the haemolysis of a blood sample is carried out. In haemolysis operation, the haemolysis device, designated as haemolysator, actually has an effect on the blood sample in order to haemolyse. This takes place, for example, by means of impact on the blood sample with ultrasound.

In accordance with one embodiment of the invention, it can be provided that detection of the measuring light values is carried out at least partly during a break in operation in the haemolysis of a blood sample. During the break in operation, there is no effect of the haemolysis device supporting the haemolysis of the blood sample. The ultrasound impact is, for example, interrupted. Combined recording of the measuring light values can also be provided during haemolysis operation on the one hand and the break in operation on the other. Depending on the observed progress of haemolysis, the following method steps can be selected. If for example, it is established that further haemolysis progress cannot be observed, there is the possibility to submit the haemolysed sample now to further determination, for example, to photometric determination of the haemoglobin derivates. Determination of the degree of haemolysis can also follow in order then to decide whether subsequent haemolysis should be carried out which, for its part, can be observed in the course of progress.

A further embodiment of the invention can provide that detection of the measuring light values is carried out, at least partly, during the effect of one or more reagents supporting the haemolysis of the blood samples. It can also be provided that haemolysis is carried out both by means of one or more reagents and by means of ultrasound impact. In haemolytic terms, functioning surfactants such as Triton X-100 in diluted form, TWEEN 621 and BRIJ (available from Sigma Aldrich) can be used as reagents.

A typical further embodiment of the invention provides that detection of the measuring light values is carried out at least partly during a period in which the blood sample is free from the effect of one or more reagents supporting haemolysis of the blood sample. The blood sample is free of the effect of one or more reagents when its haemolysing effect is used up or inhibited.

After a measurement, further reagents can be added optionally, in particular for subsequent haemolysis.

A typical further embodiment of the invention provides that intensity measuring values for measuring light values are detected for the measuring light.

A convenient variant of the invention provides that after determining completion of haemolysis, haemoglobin values of the blood sample are determined by means of an optical measuring method. Such optical methods are as such known in various forms of execution. The optical measuring components are partly used here, for example, the measuring light source and/or detector device which are used for determining haemolysis progress. A meaningful form of the invention provides that a blood sample is haemolysed by means of a haemolysis device for example by means of ultrasound haemolysis while for the haemolysis a measure is determined for the haemolysis progress and, after conclusion of haemolysis, an oximetry measurement, for example, determination of haemoglobin values of the blood sample is carried out. For oximetry measurement by means of an optical measuring method, various forms of execution are known. Haemolysis, the haemolysis test and oximetry measurement are typically carried out with the same sample in the same measuring cell. The advantage lies in that any contamination of the sample between the method steps is ruled out.

In the following, advantageous variants are explained in connection with determination of the measure for the haemolysis degree of the blood sample.

An advantageous embodiment provides that, in the comparison, local curve gradient values for target absorption values from the at least one target absorption spectrum which are spectrally assigned for one another and measuring absorption values from the at least one measuring absorption spectrum are compared. Incomplete haemolysis leads, in comparison to the target absorption spectrum, which represents a completely haemolysed blood sample, to changes in the measuring absorption spectrum. This includes first of all an increase in the absorption spectrum due to lifting absorption bands by an offset dependent on the degree of haemolysis. In addition, differences in the edge steepness in areas of low absorption are shown. Furthermore, the signal-to-noise ratio for higher haemolysis degrees is improved which is the reason why the pixel-pixel noise is sensitive for the haemolysis quality. These indicators can be taken individually or in combination to determine a measure for the haemolysis degree. The local curve increase values display in particular differences in the edge steepness. The noise behaviour is also indicated by this. The values determined from the comparison can optionally be further processed which includes in particular a mean or summation or also weighting of the values.

Typically, a further embodiment of the invention provides that, in the comparison, the target absorption values for the at least one target absorption spectrum which are spectrally assigned to one another and measuring absorption values from the at least one measuring absorption spectrum are compared. The comparison of absorption values spectrally assigned to one another can, in particular, be executed as a subtraction formation so that so-called residues are determined. They are related to the more or less formed and previously described offset lifting dependent on the haemolysis degree. Also in connection with these comparative values, further processing can be provided optionally.

In accordance with yet another embodiment of the invention, it can be provided for which at least one target absorption, a formed model absorption spectrum is used by means of absorption band summation. Such a target absorption spectrum is formed in that, for the expected components of each of the known absorption bands in the interesting spectral area, summation takes place so that a total absorption spectrum develops. Usually, the absorption bands are added in a linear manner.

A further embodiment of the invention provides that, for the at least one target absorption spectrum, a measured calibration absorption spectrum is used. The measured calibration absorption spectrum can be determined experimentally for a with surety haemolysed blood sample. It can also be provided in a form that both the model absorption spectrum and the measured calibration absorption spectrum are taken for determination of the measure of the haemolysis degree.

A typical further embodiment of the invention provides that, with the information signal, a quality control measure is displayed for a test quality of the blood sample. In particular in the clinic environment, determination of the measure for the haemolysis degree of a blood sample can also be used for determining the still or no longer existing quality of a blood sample. Depending on the application purpose, the quality control measure can, in the case of exceeding or falling short of a given threshold measure, show that an examined blood sample is still or no longer usable, for example, because aging is too far advanced.

In accordance with yet still another embodiment of the invention, it can be provided that subsequent haemolysis of the blood sample is started if the measure for the haemolysis degree falls short of a given threshold value measure. Independent of whether subsequent haemolysis is carried out or not, it can be provided that, with the output device, a signal is generated which effects a display of the achievement of a threshold haemolysis degree. Such signalling can take place in acoustic and/or visual form. For example, a corresponding display can draw the attention of the user to this. If the threshold value measure, on the other hand, is not reached, this can also be reported to the user. The installation device can, in this case, automatically generate a control signal which is given to the haemolysator used for the haemolysis to initiate a subsequent haemolysis in that, for example, the blood sample is impacted once again with ultrasound. Then, the measure for the haemolysis is determined once again to decide again whether the haemolysis has been carried out sufficiently. In this manner, an automatic control loop is implemented with which, in dependence on the measure for the haemolysis degree, operation of the haemolysis is controlled.

In the case of continued formation of determination of the measure for the haemolysis degree of the blood sample, it can be provided that a haemolysis progress is determined in which the measuring light reflected by the measuring light source during haemolysis is radiated on to the blood sample, measuring light values are detected with a detector device for measuring points of time transmitted through the blood sample and/or measuring light reflected by the blood sample and, with the evaluation device, several of the measuring light values are compared for various measuring points of time and, from this, a measure for the haemolysis progress is determined. Determination of the haemolysis degree measure of the blood sample can be carried out in time for haemolysis progress determination. But also use following progress determination can be provided. In this manner, an additional final control is enabled. In another form, the measure for haemolysis is used in the operating breaks of the haemolysis device as a type of interim information concerning haemolysis. In addition, determination of the haemoglobin values of the blood sample can be provided by means of an optical measuring method.

In connection with various embodiments of the instant device for determination of the haemolysis of a blood sample, the explanations given in connection with the method for determination of the haemolysis apply correspondingly. The device for determining haemolysis can be configured in accordance with the various method forms.

Figure 1:
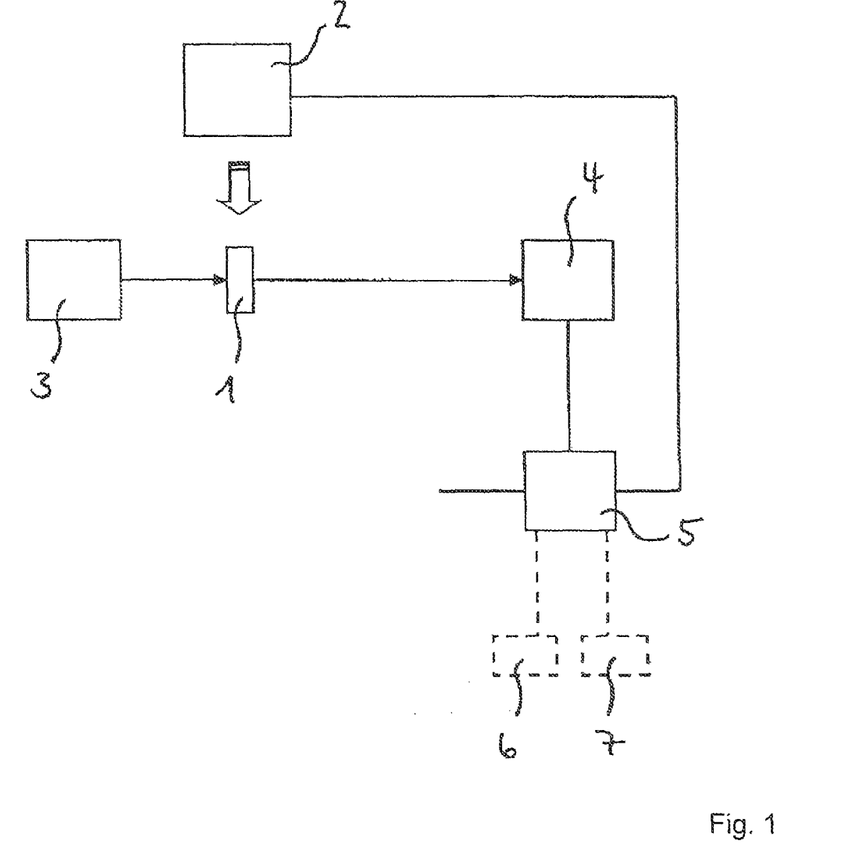
FIG. 1 is a schematic illustration of a device in accordance with the present invention for determination of haemolysis of a blood sample.

FIG. 1 shows a schematic illustration of a device in accordance with an embodiment of the invention for determination of the haemolysis of a blood sample. For haemolysis, the blood) sample located in a measuring chamber 1 is impacted by ultrasound in the presented execution example by an ultrasound device 2. The measuring light is reflected from a light source 3, which can reflect the light with a broadband spectrum or single-colour light of various wave lengths to the measuring chamber. Transmitted measuring light then reaches a detector through the blood sample. With the aid of detector 4, intensity measuring values are recorded for the transmitted measuring light, optionally in spectrally resolved form. Detector 4 is connected to an evaluator 5 by means of which the recorded measuring light values can be evaluated for determination of a transmission and/or absorption. Supplementarily or alternatively, a detector (not shown) can be provided which is configured to measure light reflected from the blood sample in the measuring chamber 1 for determination of the haemolysis progress.

In accordance with FIG. 1, the evaluator 5 is, in addition, coupled with the ultrasound device 2 so that this can be controlled depending on the evaluation result.

By means of dashed lines, an optional output device 6 is shown in FIG. 1 through which audio and/or video signals can be outputted displaying the evaluation results. Furthermore, an input device 7 is provided through which user input is recorded.

For the execution example presented in FIG. 1, the detector 4 is used together with the evaluator 5 for determination of the haemolysis progress of haemolysis of the blood sample and for determination of a measure for the haemolysis degree of the blood sample. Alternatively, separate formation of the two measuring systems can be provided so that they can be integrated individually or in combination in a haemolysator, for example, as an individual or integrated module.

Figure 2:
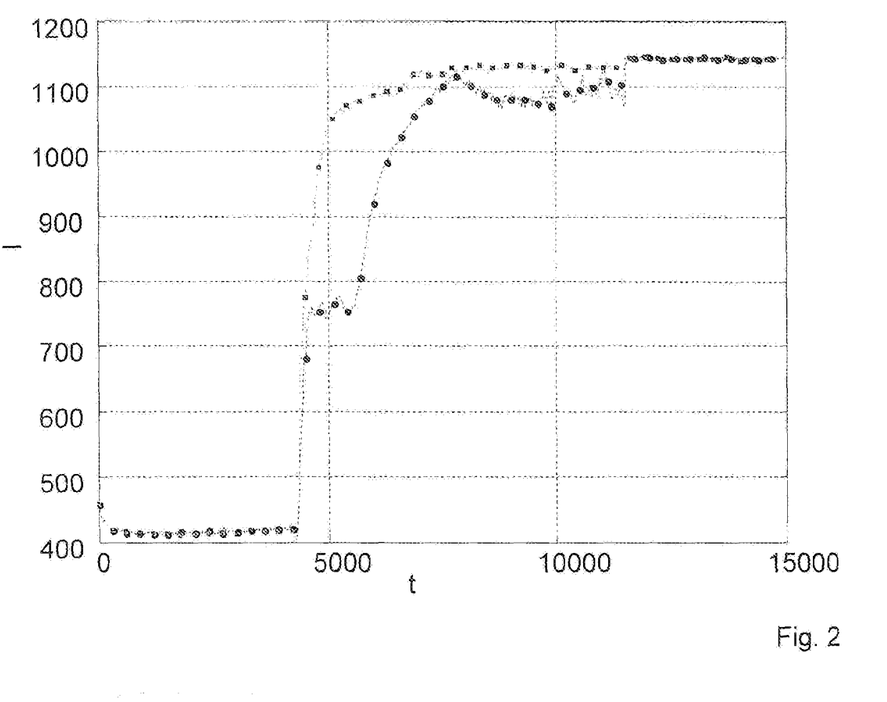
FIG. 2 is a graphic illustration for the measured intensities I (in relative units) from transmitted measuring light dependent on time t (in ms) for two different blood samples.

FIG. 2 shows graphic illustration for measuring intensity in dependence of time. The intensity detector 4 provided in FIG. 1 is used to take up this curve shape for the progress of the haemolysis of a blood sample to be determined. It turns out that, during a commencement period I (0 to about 4000 ms) in the curve shape, the measured light intensity mainly remains unchanged. Haemolysis has not yet begun. In a further curve section II (from around 4000 to around 8000 ms), the intensity of the recorded measuring light then increases displaying the beginning (at 4000 ms) and further progress of haemolysis. With progressing haemolysis, the curve shapes to a saturation section III (around 8000 to around 12000 ms) in which the transmitted measuring light intensity is scarcely changed. This displays the complete haemolysis.

The measuring curve presented by means of quadrates presents pairs of values of a blood sample for which the haemolysis course and haemolysis result was in order. The measuring curve presented by means of quadrates shows pairs of values of a blood sample for which the haemolysis shape and the haemolysis result was in order.

The time-dependent curve shape for the intensity of the transmitted measuring light can, in addition, be used to check whether air bubbles are formed during haemolysis which lead to a changed curve shape. Air bubbles lead to an abrupt increase in the transmitted measuring light as absorption and dispersion do not take place. In addition, there can also be a focus on the measuring light through the air bubbles. A non-desired local gradient in the measuring curve develops.

On the basis of the progress shape of the haemolysis in accordance with FIG. 2, it can be decided then for example whether a first of all provided haemolysis has to be extended or not. It can also be decided whether, if necessary, the haemolysis method is repeated.

Figure 3:
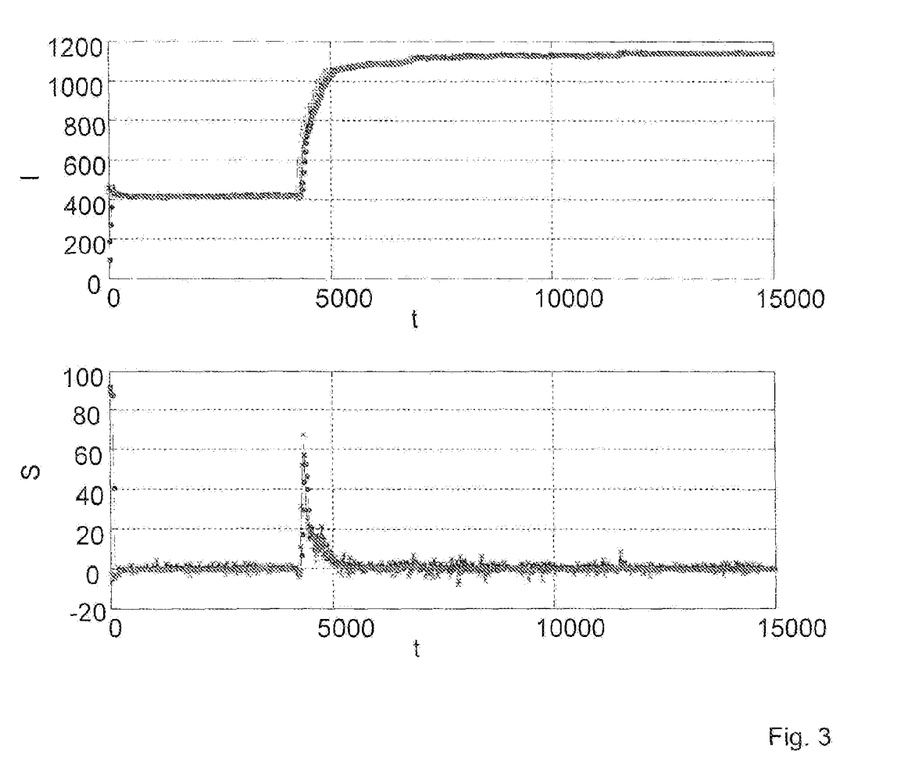
FIG. 3 is a graphic illustration of a curve shape of intensity I (in relative units) of transmitted measuring light (above) and the first derivation S (in relative units) characterising the curve gradient, each depending on the time t (in ms) whereby the haemolysis was classified as "in order"

FIG. 3 shows a graphic illustration of a curve shape for the dependence of the intensity in time on transmitted measuring light and the first derivation characterising the curve gradient whereby haemolysis was classified as "in order". Haemolysis leads to a strong noise in the recorded measuring data (raw data—crosses in FIG. 3). Noise suppression by means of filtering can be provided. The measuring data recording is simplified by this. These filtered data are depicted in the diagram s circles. Classification of haemolysis was carried out depending on the time position of a last significant curve gradient. This is apparent when the curve gradient lies above the threshold value. Such measuring values are presented in the upper part diagram in addition by open quadrates. When the last significant curve gradient lies within a valid time window, the haemolysis is in order. Haemolysis is classified as "borderline" (see FIG. 4 below) when the last significant curve gradient lies at the edge of the time window. Haemolysis is not "in order" when the last significant curve gradient lies outside the time window.

Figure 4:
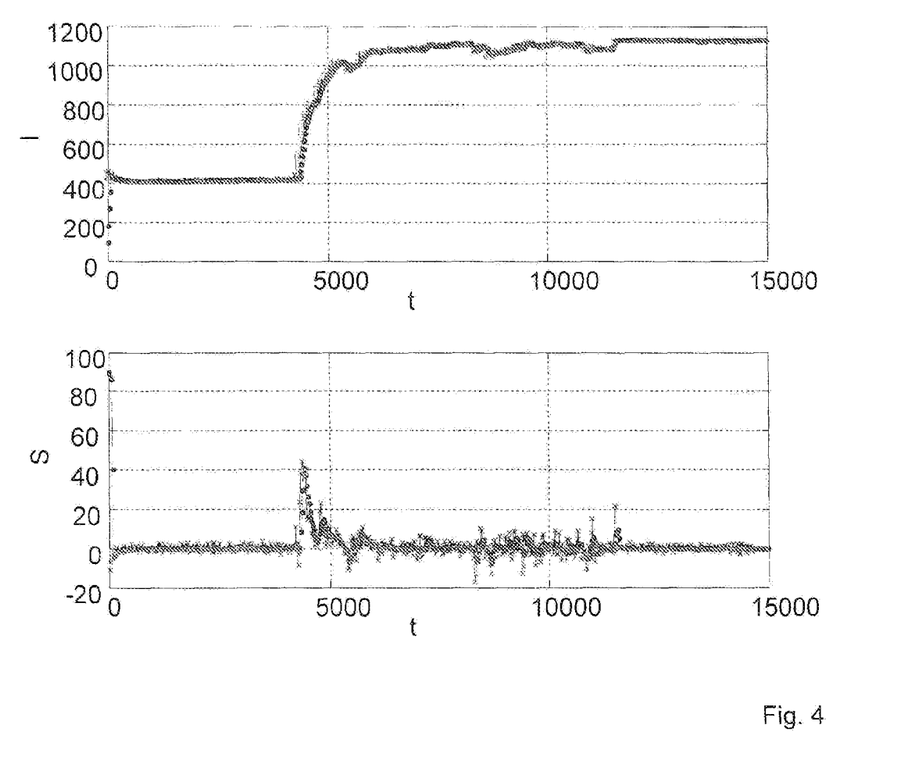
FIG. 4 is a graphic illustration of intensity I (in relative units) of transmitted measuring light (above) and the first derivation S (in relative units) characterising the curve gradient of these each depending on the time t (in ms) whereby haemolysis was classified as "borderline"

FIG. 4 shows a graphic illustration of a curve shape for the dependence of intensity in time on transmitted measuring light and the first derivation characterising the curve gradient whereby haemolysis was classified as "borderline".

Figure 5:
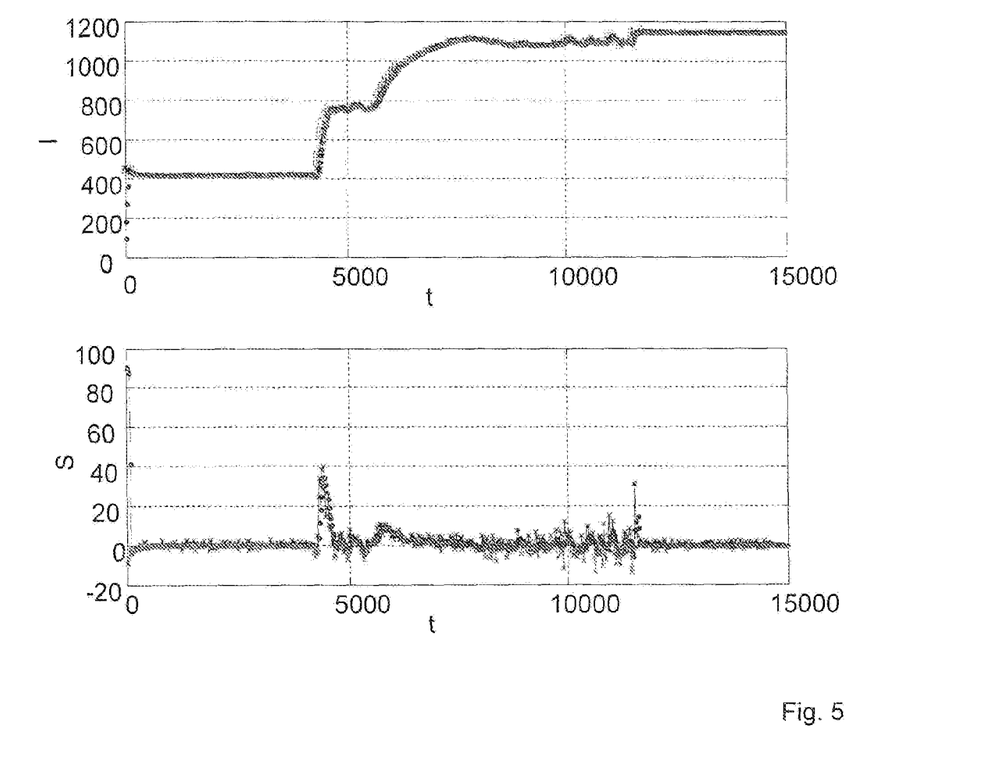
FIG. 5 a graphic illustration of a curve shape of intensity I (in relative units) of transmitted measuring light (above) and the first derivation S (in relative units) characterising the curve gradient, each depending on the time t (in ms) whereby haemolysis was classified as "not in order".

FIG. 5 shows a graphic illustration of a curve shape for the dependence of the intensity in time on transmitted measuring light and the first derivation characterising the curve gradient the haemolysis being classified as "not in order".

Figure 6:
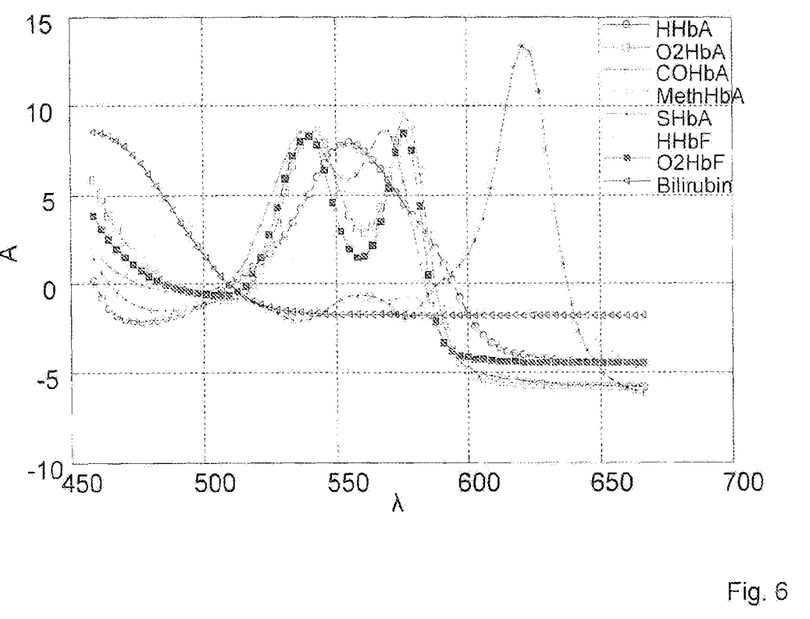
FIG. 6 is a graphic illustration of absorption A (in mmol $cm^{-1}$ $L^{-1}$) depending on the wave length $\lambda$ (in nm) for the individual absorption bands of haemoglobin derivates and the degradation product bilirubin.

FIG. 6 shows a graphic illustration of the absorption depending on the wave length for the individual absorption bands of haemoglobin derivates and the degradation product bilirubin. By means of summation of the absorption bands for the substances presented, a model absorption spectrum results which is compared in determination of the measure for the haemolysis degree with a measured measuring absorption spectrum for a blood sample to be examined. The target absorption spectrum taken in determination of the measure for the haemolysis degree can be gained alternatively by examining a calibration blood sample spectroscopically for which the haemolysis degree is known to be reliable. If, for example, haemolysis for the calibration blood sample is carried out completely, a calibration absorption spectrum results for a 110 percent haemolysis degree.

Figure 7:
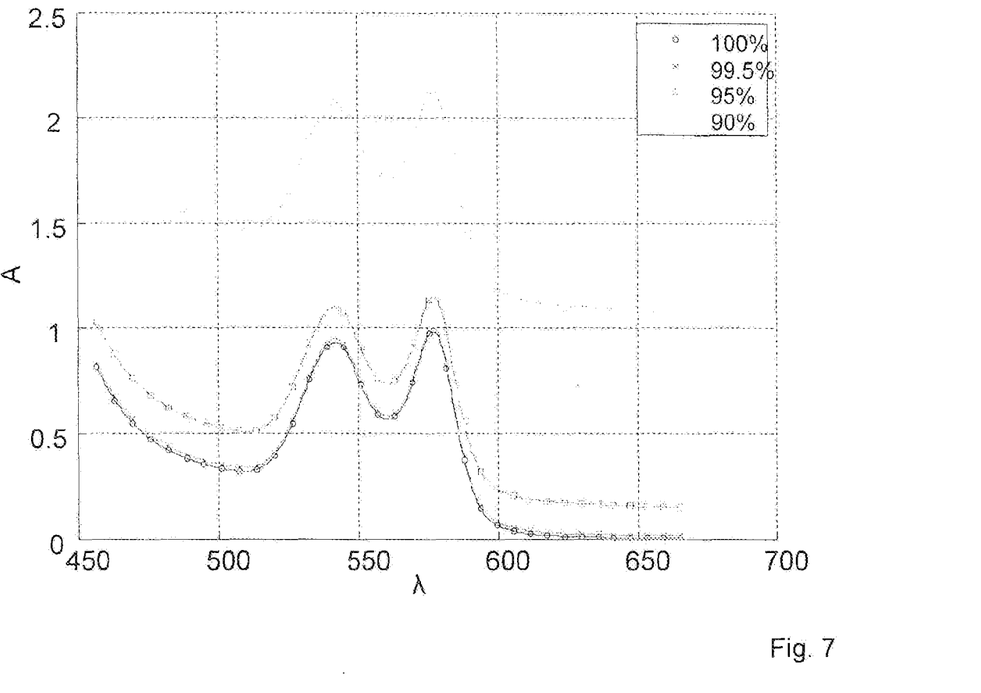
FIG. 7 is a graphic illustration of the absorption A concerned (in relative units) for several measuring absorption spectrums depending on the wave length $\lambda$ (in nm) of a blood sample for various haemolysis degrees.

FIG. 7 shows a graphic illustration for several absorption spectrums of a blood sample for various haemolysis degrees which are shown on the top right.

Figure 8:
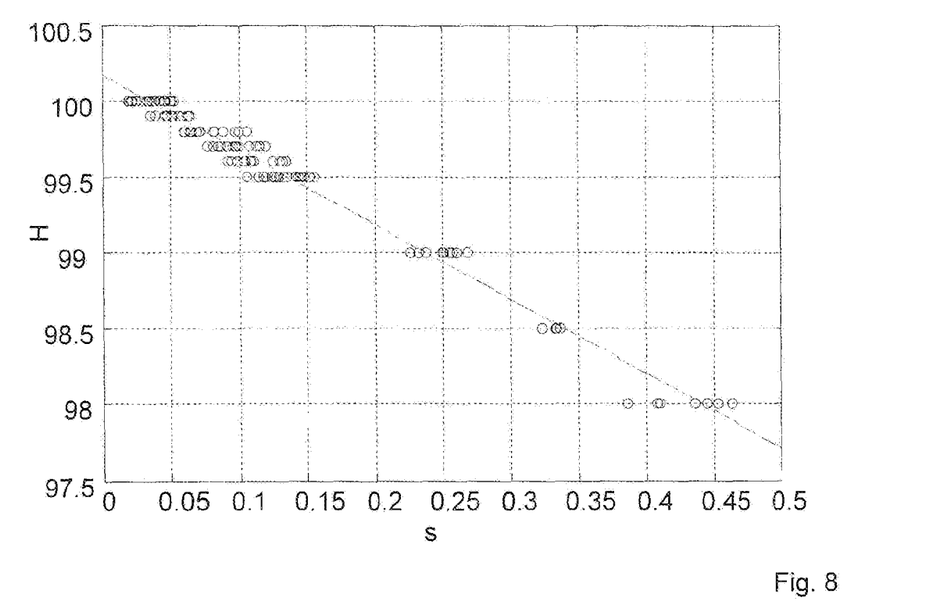
FIG. 8 is a graphic illustration for the assignment between haemolysis degree H (in %) and the determined curve gradients (in relative units) in measuring absorption spectrums for several blood samples.

FIG. 8 shows a graphic illustration for the assignment between haemolysis degree and the determined curve gradient in measuring absorption spectrums for several blood samples. It turns out that the connection between the haemolysis degree and curve gradient can be described by means of a straight equation (in German sometimes linear "fitgerade"). For the comparison, samples were produced with a firmly set haemolysis degree in that specifically quantities of haemolysed blood and non-haemolysed blood were mixed with one another. As an additional control, the erythrocytes were counted under a microscope. The values presented in FIG. 8 for the curve gradient were determined in that, for the wave lengths in the area examined, local gradients assigned to one another for an absorption curve of a sample with a 100 percent haemolysis degree on the one hand and a measuring curve with a 100 percent different haemolysis degree on the other were compared with one another and a report drawn up for the differences established thereby.

Figure 9:
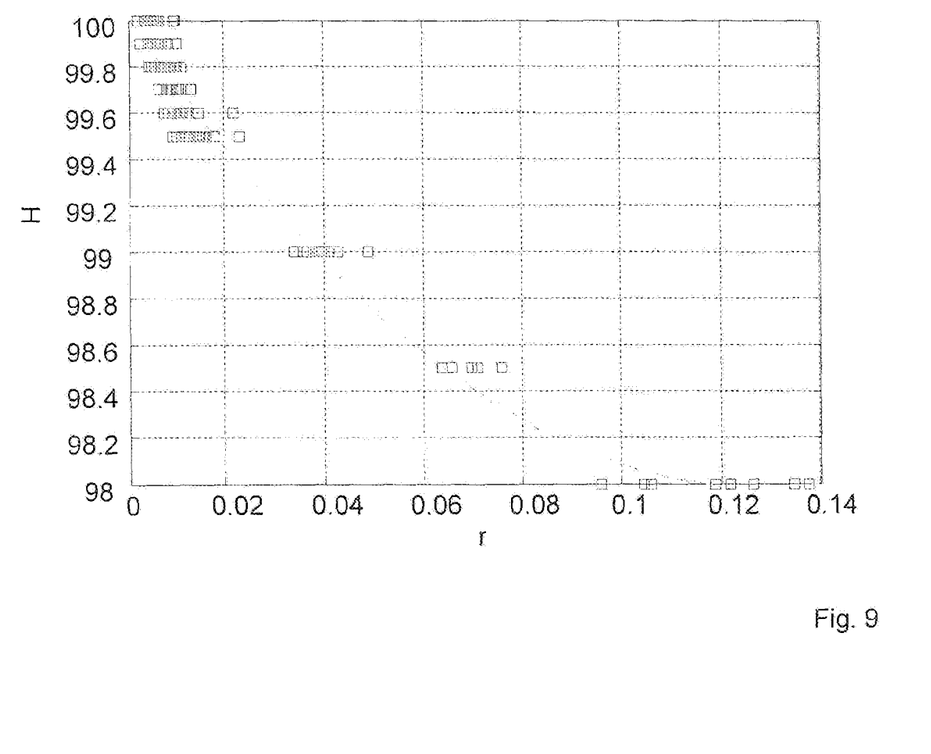
FIG. 9 is a graphic illustration for the assignment between haemolysis degree H (in %) and the so-called residues r (in relative units) in measuring absorption spectrums for several blood samples.

FIG. 9 shows a graphic illustration for the assignment between haemolysis degree and so-called residues for several blood samples. A quadratic connection between the haemolysis degree and the residues (quadratic fit functions) arises. The residues are a measure for the congruence of the adaptation curves found by means of regression with the experimentally measured values.

Figure 10:
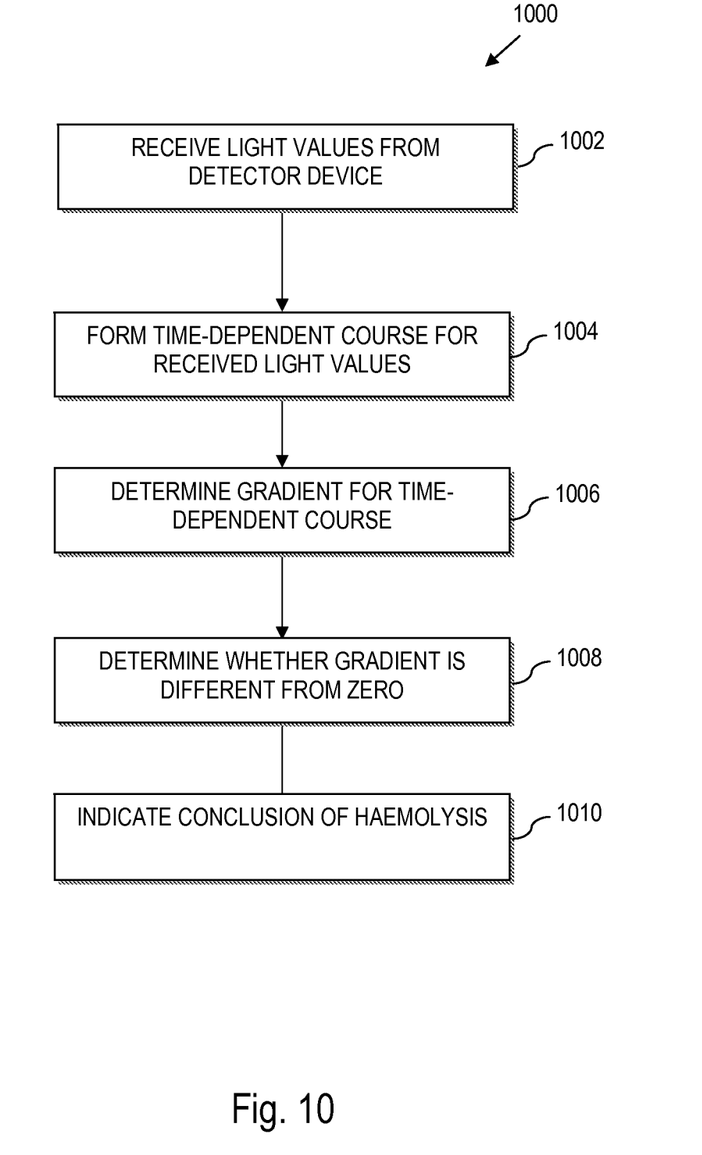
FIG. 10 is a flow chart showing an algorithm performed by an evaluation device, according to various aspects of the present disclosure.

FIG. 10 illustrates an algorithm 1000 performed by the evaluation device (5 from FIG. 1). At 1002, the evaluation device receives light values from the detector device (4 of FIG. 1). The evaluation device compares several received light values for different points of time and determines a measure of the haemolysis progress. More particularly, the evaluation device performs the comparison by forming a time-dependent course for the received light values at 1004 and determining for the time-dependent course, at least section-wise, a gradient of an assigned measuring curve as a comparative measure for the comparison of the measuring light values at the different measuring points of time at 1006. At 1008, the evaluation device determines whether the gradient is different from zero, and at 1010, the evaluation device indicates a conclusion of haemolysis. For instance, the evaluation device indicates a conclusion of the haemolysis when the gradient within a selectable measuring accuracy, after a measuring period in which the gradient is different from zero, falls to a minimum going down to zero process when the gradient approaches zero after the gradient was different from zero for a predetermined time.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modifications and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for determining the haemolysis of a blood sample, the method comprising:
   irradiating measuring light on the blood sample after a haemolysis operation on the blood sample has been started, which measuring light is radiated from a measuring light source;
   detecting measuring light values from the measuring light source at several measuring points of time for measuring at least one of light transmitted through and light reflected by the blood sample with a detector device;
   comparing several of the measuring light values for different measuring points of time and determining a measure for the haemolysis progress by an evaluation device by receiving the measuring light values detected by the detector device, forming a time-dependent course of light values for the received measuring light values, determining for the time-dependent course at least section-wise a gradient in an assigned measuring curve as a comparative measure for the comparison of the measuring light values at the different measuring points of time, and determine when the gradient is different from zero; and
   determining the conclusion of the haemolysis when the gradient within a selectable measurement accuracy, after a measuring period in which the gradient is different from zero, falls to a minimum going down to zero.

2. The method in accordance with claim 1, wherein detection of the measuring light values is carried out at least partly during the haemolysis operation of a haemolysis device used for the haemolysis of a blood sample.

3. The method in accordance with claim 1, wherein the detection of the measuring light values is carried out at least partly during an operation break of the haemolysis device used for the haemolysis of a blood sample.

4. The method in accordance with claim 1, wherein the detection of the measuring light values is carried out at least partly during the effect of one or more reagents supporting the haemolysis of the blood sample.

5. The method in accordance with claim 1, wherein the detection of the measuring light values is carried out at least partly during a period in which the blood sample is free from the effect of one or more reagents supporting the haemolysis of the blood sample.

6. The method in accordance with claim 1, wherein intensity measuring values are detected as measuring light values for the measuring light.

7. The method in accordance with claim 1, wherein after determining the conclusion of the haemolysis, haemoglobin values of the blood sample are determined by an optical measuring method.

8. A device that determines the haemolysis of a blood sample, the device comprising:
   a measuring light source which is configured to irradiate measuring light on the blood sample after a haemolysis operation on the blood sample has been started;
   a detector device which is configured to detect measuring light values from the measuring light source at several measuring points of time, for measuring at least one of light transmitted through the blood sample and light reflected by the blood sample; and
   an evaluation device which is configured to:
      receive the measuring light values detected by the detector device;
      form a time-dependent course of light values from the received measuring light values;
      determine at least section-wise, a gradient for an assigned measuring curve from the time-dependent course, as a comparative measure for a comparison of the measuring light values at the different measuring points of time;
      determine when the gradient is different from zero; and
      indicate a conclusion of the haemolysis when the gradient within a selectable measuring accuracy after a measuring period of time, in which the gradient is different from zero, falls to a minimum going down to zero.

9. The device in accordance with claim 8, further comprising:
   a haemolysator that performs haemolysis on the blood sample.

* * * * *